US00PP16650P2

(12) United States Plant Patent
Utecht

(10) Patent No.: US PP16,650 P2
(45) Date of Patent: Jun. 13, 2006

(54) *GERANIUM* PLANT NAMED 'FISHIMRED'

(50) Latin Name: *Pelargonium zonale*
Varietal Denomination: Fishimred

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 82 days.

(21) Appl. No.: 10/998,599

(22) Filed: Nov. 30, 2004

(51) Int. Cl.
*A01H 5/00* (2006.01)

(52) U.S. Cl. ..... Plt./330
(58) Field of Classification Search ..... Plt./330, Plt./325
See application file for complete search history.

(56) References Cited
PUBLICATIONS
German PBR Application No. PEL 1904 filed Jun. 4, 2003 (Copy of German Gazettes dated 1) Jul. 15, 2003—Listing Assigned Application for Protection No. (2 pgs), and 2) May 15, 2004—Publishing Proposed Variety Denomination (2 pgs)).
Canadian PBR Application No. 03–3904 filed Nov. 21, 2003 (Copy of Canadian Plant Varieties Journal dated Jan., 2004 Listing Assigned Application Number (2 pgs).

*Primary Examiner*—Kent Bell
(74) *Attorney, Agent, or Firm*—Foley & Lardner LLP

(57) ABSTRACT

A new and distinct cultivar of *geranium* plant named 'Fishimred' particularly characterized by the combined features of bright, orange-red, semi-double flowers; wide inflorescences on long, dark red peduncles; medium-sized, deep-green foliage with weak zonation; vigorous growth, and a tall, rounded plant habit; medium to late spring flowering response; and suitable for landscaping even under less than optimal conditions.

1 Drawing Sheet

Genus and species of the plant claimed: *Pelargonium zonale* L'Héritier (hybrid).
Variety denomination: 'Fishimred'.

BACKGROUND OF THE INVENTION

The present invention comprises a new and distinct cultivar of *geranium*, botanically known as *Pelargonium zonale,* and hereinafter referred to by the cultivar name 'Fishimred'.

'Fishimred' is a product of a planned breeding program which had the objective of creating new zonal *geranium* cultivars with red flower color, dark-green, zoned foliage, and vigorous growth.

'Fishimred' originated from a hybridization made by the inventor, Angelika Utecht, in a controlled breeding program in Hillscheid, Germany, in 1999. The female parent was the unpatented variety 'Fisnida', having orange, single-type flowers, large inflorescence on long, strong peduncles, medium green foliage with distinct zonation, and relatively vigorous growth. The male parent of 'Fishimred' was the patented variety 'Tango' (U.S. Plant Pat. No. 5,933), and characterized by red, semi-double flowers, dark-green leaves, without zonation, and medium sized plant habit.

'Fishimred' was selected as one flowering plant within the progeny of the stated cross by Angelika Utecht in 2000 in a controlled environment in Fuerteventura, Canary Islands, Spain. The first act of asexual reproduction of 'Fishimred' was accomplished when vegetative cuttings were taken from the initial selection in the fall of 2000 in a controlled environment in Fuerteventura, Spain, by, or under the supervision of, Angelika Utecht.

Horticultural examination of plants grown from cuttings of the plant initiated in May of 2001, in Hillscheid, Germany, and continuing thereafter, has demonstrated that the combination of characteristics as herein disclosed for 'Fishimred' are firmly fixed and are retained through successive generations of asexual reproduction.

BRIEF SUMMARY OF THE INVENTION

'Fishimred' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fishimred' in combination distinguish this *geranium* as a new and distinct cultivar:

1. bright orange-red, semi-double flowers;
2. relatively large inflorescences on long, dark red peduncles;
3. medium sized, rounded, deep-green leaves with slight zonation;
4. vigorous growth, tall and wide plant habit; and
5. about mid season spring flowering response.

Of the many commercial cultivars known to the present inventor, the most similar in comparison to 'Fishimred' is the parental variety 'Tango'.

In comparison to 'Tango', 'Fishimred' has a slightly lighter, more orange-red hue of flower, deeper red peduncles, leaves with at least weak zonation, and much taller plant habit.

BRIEF DESCRIPTION OF THE DRAWING

The accompanying photographic drawing shows typical flower and foliage characteristics of 'Fishimred' with colors being as true as possible with an illustration of this type. The photographic drawing shows a side perspective view of flowering potted plant of 'Fishimred' with leaves, buds and inflorescences.

DETAILED BOTANICAL DESCRIPTION

The measurements were taken in Hillscheid, Germany, in mid May, 11 weeks after planting of rooted cuttings. The plants were growing in 14 cm pots, they had not been pinched.

In the following description, color references are made to The Royal Horticultural Society Colour Chart. The color values were determined indoors from plants growing in a green-house in May 2003 in Hillscheid, Germany.

Parentage:
- *Male parent.*—'Tango' (U.S. Plant Pat. No. 5,933).
- *Female parent.*—Unpatented variety 'Fisnida'.

Classification: *Pelargonium zonale* L'Héritier (hybrid).
Propagation: Vegetative cuttings.
Inflorescence:
Umbel:
- *Shape.*—Almost semi-spherical, wide.
- *Average diameter.*—119 mm.
- *Average depth.*—50 mm.
- *Number of flowers and buds per umbel.*—About 50 or more.

Peduncle:
- *Peduncle length.*—145 mm.
- *Peduncle diameter.*—5 mm, relatively strong.
- *Peduncle color.*—Mainly dark red (grayish-purple group), RHS 183 C.

Pedicel:
- *Pedicel length.*—40 mm.
- *Pedicel diameter.*—2 mm.
- *Pedicel color.*—Mainly grayish-red, RHS 181 A.

Corolla:
- *Average diameter.*—48 mm.
- *Depth.*—15 mm or less.
- *Form.*—Semi-double type.
- *Shape.*—Round outline, with the upper petals about the same size as the lower petals, wide open, almost flat.
- *Number of petals.*—7–9.
- *Number of petaloids.*—None observed.

Petals:
- *Shape of petals.*—Obovate, base acute, upper end is rounded, margin is entire.
- *Size of petals.*—Upper petals: 26–28 mm long, 18–20 mm wide; lower petals: 25–26 mm long, 20 mm wide.
- *Color* (*general tonality from a distance of three meters*).—Bright orange-red.
- *Color of upper petals.*—Upper part: red, RHS 44 B, near the base red, RHS 46 C.
- *Markings of upper petals.*—Fine, dark red veins, RHS 46 A.
- *Color of lower petals.*—Red, RHS 44 B.
- *Markings of lower petals.*—None.
- *Color of lower surface of petals.*—Red, from RHS 40 A to RHS 44 B.

Sepals:
- *Color of sepals.*—Lower (visible) surface: base and main part grayish-purple, RHS 185A, the tips are green, RHS 137 D; upper/inner surface: grayish-purple, RHS 185 A and green, RHS 143 C.
- *Number of sepals.*—5.
- *Shape of sepals.*—Linear to lanceolate, acute tip, fused base, surface with very short pubescence, margin entire.
- *Size of sepals.*—10–11 mm long, 4–5 mm wide for the largest upper sepal, 3 mm in width for the other sepals.

Bud (just prior to petals unfolding):
- *Shape.*—Elliptical.
- *Color of sepals.*—Mainly green, RHS 137 D, at the base greyish-purple, RHS 185 A.
- *Color of petals.*—Red, RHS 44A to 44 B.
- *Length.*—23 mm.
- *Width.*—11 mm.

Reproductive organs:
Androecium: 5–7 fertile anthers, moderate pollen, orange, RHS N25 A, filaments white, RHS 155 D, to light-pink, RHS 52 D.
Gynoecium: One pistil, stigma 5–6-lobed, style and stigma reddish, RHS 46 C.
Fertility/seed set: Occasionally, mainly in late summer to fall.
Fruit: Oblong, about 5–6 mm wide, rostrum (beak) 38–42 mm long.
Seed: Oblong, 4–5 mm long, brown (greyed-orange), RHS 177 B.
Spring flowering response period: In Hillscheid, Germany, in 2003 plants had on average 0.2 flowers opened 8 weeks after planting of rooted cuttings.
Outdoor flower production: Continuously and moderately rich flowering, the flower count in 2003 in Hillscheid, Germany, indicated about 15–20 inflorescences per plant in late summer.
Durability: No fading of the flower color, fair rain resistance.
Lastingness of the individual flower: About 7–8 days at 18° C., about 18 days for the umbel.
Fragrance: None.
Plant:
Foliage:
- *Shape.*—Kidney-shaped, with cordate base, with the gap between the lowest lobes open to nearly closed, apex rounded with weak lobes, margin somewhat wavy.
- *Margin.*—Bicrenate.
- *Texture.*—Upper surface smooth.
- *Size of leaf.*—111 mm wide, 65 mm long.
- *Color of upper surface.*—Green, between RHS 137 A to RHS 137 B.
- *Color of zonation.*—Yellow-green, about RHS 147 A, during the summer months, the zonation may be visible on young leaves only.

*Color of lower surface.*—Yellow-green, RHS 137 D.
- *Petioles.*—65–80 mm long, 2.5 mm diameter, light green in color, approximately RHS 143 C.

General appearance and form:
- *Stem color.*—Mainly light green, RHS 143 B, in parts greyish-red), RHS 179 B.
- *Internode length.*—About 30 mm.
- *Branching pattern.*—6.0 branches.
- *Size of plants.*—Height: 18.5 cm, Spread: 26.8 cm (11-week-old plants, as described, measured from the top of the soil (base of the main stem) to the surface of the foliage canopy, without inflorescences).

I claim:

1. A new and distinct cultivar of *geranium* plant named 'Fishimred', as described and illustrated herein.

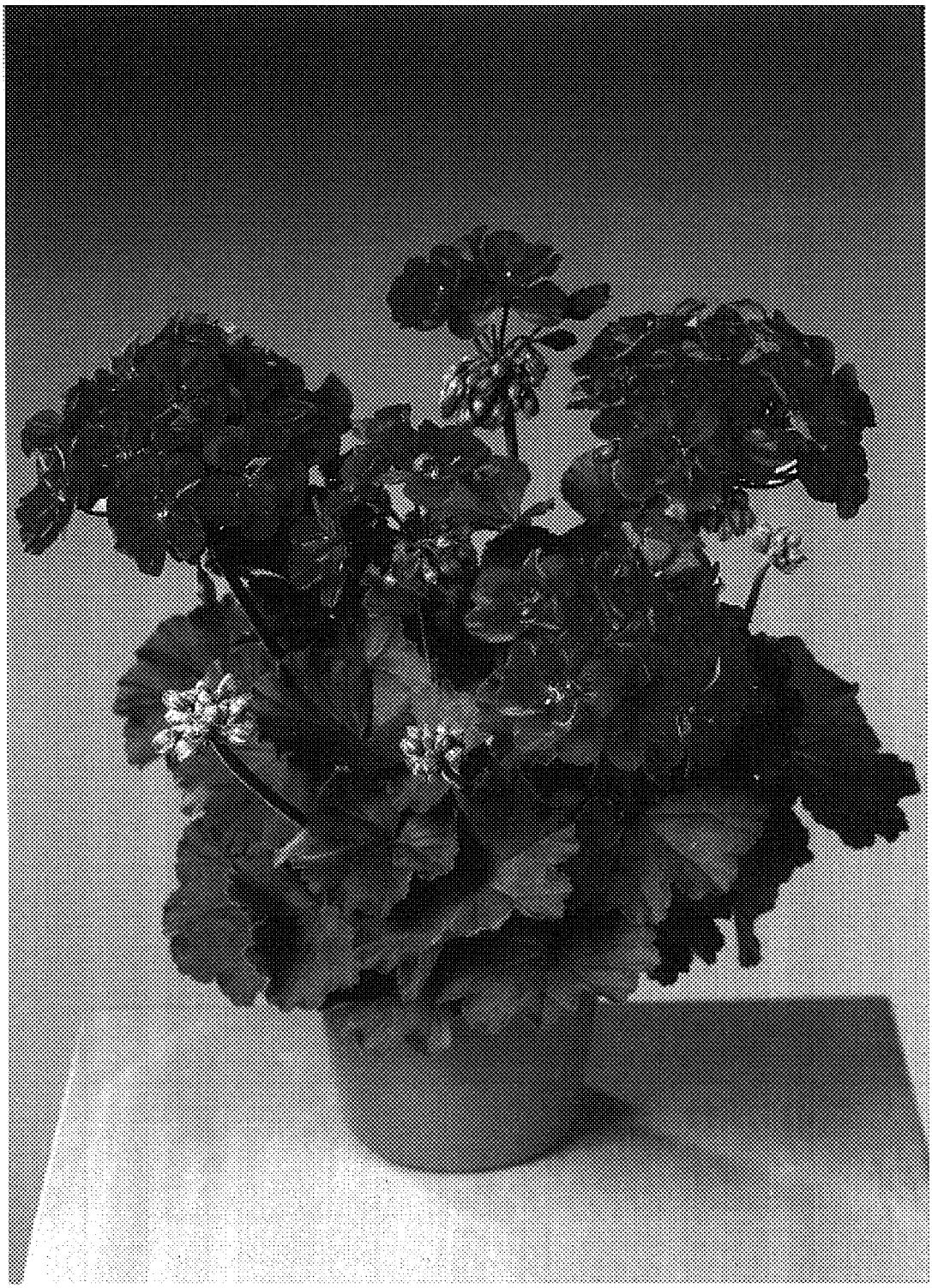

* * * * *